United States Patent
Jordan et al.

(10) Patent No.: US 9,827,312 B2
(45) Date of Patent: Nov. 28, 2017

(54) METHOD FOR CARRYING THERAPEUTIC SUBSTANCES INTO CELLS

(71) Applicant: MAGFORCE AG, Berlin (DE)

(72) Inventors: Andreas Jordan, Berlin (DE); Norbert Waldoefner, Berlin (DE); Regina Scholz, Berlin (DE)

(73) Assignee: MAGFORCE AG, Berlin (DE)

( * ) Notice: Subject to any disclaimer, the term of this patent is extended or adjusted under 35 U.S.C. 154(b) by 0 days.

(21) Appl. No.: 14/849,053

(22) Filed: Sep. 9, 2015

(65) Prior Publication Data

US 2016/0067338 A1 Mar. 10, 2016

Related U.S. Application Data

(63) Continuation of application No. 13/470,166, filed on May 11, 2012, now abandoned, which is a continuation of application No. 12/064,236, filed as application No. PCT/DE2006/001453 on Aug. 21, 2006, now abandoned.

(60) Provisional application No. 60/711,407, filed on Aug. 26, 2005.

(30) Foreign Application Priority Data

Aug. 19, 2005 (DE) ........................ 10 2005 039 579

(51) Int. Cl.
| | |
|---|---|
| A61K 9/50 | (2006.01) |
| A61K 9/51 | (2006.01) |
| A61K 33/00 | (2006.01) |
| A61K 41/00 | (2006.01) |
| A61K 9/00 | (2006.01) |
| A61K 9/10 | (2006.01) |
| A61K 33/24 | (2006.01) |
| A61K 33/26 | (2006.01) |
| A61K 33/30 | (2006.01) |
| A61K 33/32 | (2006.01) |
| A61K 33/34 | (2006.01) |
| A61K 45/06 | (2006.01) |
| A61N 1/40 | (2006.01) |
| B82Y 5/00 | (2011.01) |
| A61K 31/136 | (2006.01) |
| A61K 31/282 | (2006.01) |
| A61K 31/407 | (2006.01) |
| A61K 31/513 | (2006.01) |
| A61K 31/546 | (2006.01) |

(52) U.S. Cl.
CPC ........ *A61K 41/0052* (2013.01); *A61K 9/0009* (2013.01); *A61K 9/0019* (2013.01); *A61K 9/10* (2013.01); *A61K 9/5094* (2013.01); *A61K 9/5115* (2013.01); *A61K 9/5146* (2013.01); *A61K 31/136* (2013.01); *A61K 31/282* (2013.01); *A61K 31/407* (2013.01); *A61K 31/513* (2013.01); *A61K 31/546* (2013.01); *A61K 33/00* (2013.01); *A61K 33/24* (2013.01); *A61K 33/26* (2013.01); *A61K 33/30* (2013.01); *A61K 33/32* (2013.01); *A61K 33/34* (2013.01); *A61K 45/06* (2013.01); *A61N 1/406* (2013.01); *B82Y 5/00* (2013.01); *Y10S 977/773* (2013.01)

(58) Field of Classification Search
None
See application file for complete search history.

(56) References Cited

U.S. PATENT DOCUMENTS

| | | | |
|---|---|---|---|
| 5,411,730 A | | 5/1995 | Kirpotin et al. |
| 5,554,638 A | | 9/1996 | Dewhirst et al. |
| 5,935,275 A | | 8/1999 | Burgard et al. |
| 6,147,205 A | | 11/2000 | McGall et al. |
| 6,162,498 A | | 12/2000 | Mennig et al. |
| 6,183,658 B1 | | 2/2001 | Lesniak et al. |
| 6,541,039 B1 | * | 4/2003 | Lesniak ............ A61K 41/0052 424/422 |
| 6,669,623 B1 | | 12/2003 | Jordan |
| 7,393,685 B1 | | 7/2008 | Jordan |
| 7,530,940 B2 | | 5/2009 | Hainfeld et al. |
| 2002/0103517 A1 | | 8/2002 | West et al. |
| 2003/0201208 A1 | | 10/2003 | Koch et al. |

(Continued)

FOREIGN PATENT DOCUMENTS

| | | |
|---|---|---|
| CN | 1260724 A | 7/2000 |
| DE | 195 15 820 | 10/1996 |

(Continued)

OTHER PUBLICATIONS

M Ma, Y Zhang, W Yu, H-Y Shen, H-Q Zhang, N Gu. "Preparation and characterization of magnetite nanoparticles coated by amino silane." Colloids and Surfaces A: Physicochemical Engineering Aspects, vol. 212, 2003, pp. 219-226.*

(Continued)

*Primary Examiner* — Isaac Shomer
(74) *Attorney, Agent, or Firm* — The Marbury Law Group, PLLC

(57) ABSTRACT

The present invention relates to compositions containing nanoparticles and uses of said composition for transferring therapeutically active substances into cells by means of specifically coated nanoparticles. The chemical design of the particles is such that a large amount thereof is absorbed into the cells. No direct bond between nanoparticle and the therapeutically active substance is required for the transfer into the cells. Thanks to said transfer, an increased efficacy of the substance and simultaneously reduced systemic toxicity is achieved, i.e. an increase in the efficacy while the side effects are reduced.

8 Claims, 7 Drawing Sheets

(56) References Cited

U.S. PATENT DOCUMENTS

| | | | |
|---|---|---|---|
| 2005/0058603 A1 | 3/2005 | Gao et al. | |
| 2005/0084539 A1 | 4/2005 | Handa et al. | |
| 2005/0090732 A1* | 4/2005 | Ivkov | A61N 1/406 600/411 |
| 2008/0187595 A1 | 8/2008 | Jordan et al. | |
| 2008/0268061 A1 | 10/2008 | Jordan et al. | |
| 2012/0225128 A1 | 9/2012 | Jordan et al. | |

FOREIGN PATENT DOCUMENTS

| | | |
|---|---|---|
| DE | 196 14 136 | 10/1997 |
| DE | 197 26 282 A1 | 12/1998 |
| DE | 199 12 798 | 2/2000 |
| DE | 199 40 220 A1 | 2/2001 |
| DE | 100 20 376 A1 | 11/2001 |
| DE | 100 59 151 | 6/2002 |
| EP | 1 162 955 A1 | 12/2001 |
| EP | 1 284 307 | 2/2003 |
| JP | 2002-507964 | 3/2002 |
| JP | 2003-507434 | 2/2003 |
| JP | 2004-305055 A | 11/2004 |
| WO | WO 02/43708 A2 | 6/2002 |
| WO | WO 2006/089290 A1 | 8/2006 |

OTHER PUBLICATIONS

X Liu, Z Ma, J Xing, H Liu. "Preparation and characterization of amino-silane modified superparamagnetic silica nanospheres." Journal of Magnetism and Magnetic Materials, vol. 270, 2004, pp. 1-6.*

I Koh. "Functionalization of Nanoparticles for Biological Applications." University of Maryland PhD Thesis, 2005, pages: three initial pages, pp. i-xi, and pp. 1-186 (200 total sheets).*

L Labios. "Nanobowls Offer a Way to Magnetically Deliver Drugs in the Body." UC San Diego News Center. http://ucsdnews.ucsd.edu/pressrelease/nanobowls_offer_a_way_to_magnetically_deliver_drugs_in_the_body, accessed Mar. 28, 2017, initially published Aug. 3, 2006, 3 pages.*

Alas et al., "Potentiation of Fludarabine Cytotoxicity on non-Hodgkin's Lymphoma by Pentoxifylline and Rituximab," Anticancer Research, 2000, vol. 20, pp. 2961-2966.

Bruce et al., "Surface Modification of Magnetic Nanoparticles with Alkoxysilanes and Their Application in Magnetic Bioseparations," Langmuir, 2005, vol. 21, No. 15, pp. 7029-7035.

Budd et al., "Randomized Trial of Carboplatin plus Amifostine versus Carboplatin Alone in Patients with Advanced Solid Tumors," Cancer, Sep. 1997, vol. 80, No. 6pp. 1134-1140.

Bull J.M.C., "An Update on the Anticancer Effects of a Combination of Chemotherapy and Hyperthermia," Cancer Research (Suppl.), Oct. 1984, vol. 44, pp. 4853s-4856s.

Gneveckow et al., "Description and characterization of the novel hyperthermia- and thermoablation-system MFH 300F for clinical magnetic fluid hyperthermia," Med. Phys., Jun. 2004, vol. 31, No. 6, pp. 1444-1451, abstract only.

Hidaka et al., "Differential Control of Synergistic Effect with Polyene Macrolide Antibiotics upon Chinese Hamster Cells in Vitro," Cancer Research, Dec. 1978, vol. 38, pp. 4650-4653.

Ito et al., Medical Application of Functionalized Magnetic Nanoparticles, J. Bioscience and Bioengineering, 2005, vol. 100, No. 1, pp. 1-11.

Jain et al., "Iron Oxide Nanoparticles for Sustained Delivery of Anticancer Agents," Molecular Pharma., 2005, vol. 2, No. 3, pp. 194-205.

Kohler et al., "Methotrrexate-modified superparamagnetic nanoparticles and their intracellular uptake into human cancer cells," Langmuir, Sep. 2005, vol. 21, No. 19, pp. 8858-8864, abstract only.

Ma et al., "Preparation and characterization of magnetite nanoparticles coated by amino silane," Colloids and Surfaces A: Physiochem. Eng. Aspects, 2003, vol. 212, pp. 219-226.

Masai et al., "Development of Anticancer-Agent-Releasing Microcapsules for Chemotherapy Combined with Embolo-Hyperthermic Therapy," Nippon Acta Radiologica, 1995, vol. 55, No. 1, pp. 50-57, with abstract.

Nakashima et al., "Potentiation of Bleomycin by an Antifungal Polyene, Pentamycin, in Transformed Animal Cells," Cancer Research, Dec. 1974, vol. 34, pp. 3258-3261.

Ohishi et al., "Potentiation of antitumor and antimetastatic activities of adriamycin by a novel N-alkylated dihydropyridine, AC394, and its enantiomers in colon cancer-bearing mice," Cancer Chemother. Pharmacol., 1996, vol. 38, pp. 446-452.

Ronzheimer M., MagForce Nanotechnologies gewinnt renommierten Frost & Sullivan Technologiepreis, BerliNews: Revolutionäre Nano-Krebstherapie, Oct. 2005, vol. 5, pp. 1-5, www.berlinews.de/archiv-2004/3754.shtml, Article in German.

* cited by examiner

METHOD FOR CARRYING THERAPEUTIC SUBSTANCES INTO CELLS

The present invention relates to compositions containing nanoparticles and uses of said composition for transferring therapeutically active substances into cells, in particular cancer cells. The chemical design of the particles is such that a large amount thereof is absorbed into the cells. No direct bond between nanoparticle and the therapeutically active substance is required for the transfer into the cells. The pharmaceutical compositions consisting of nanoparticle and anti-cancer drug lead to an increased efficacy of the anti-cancer drug as well as to reduced side effects.

It is known that nanoparticles can be absorbed by cells (in particular tumor cells) by means of endocytosis. A method for the preparation of cell-internizable nanoparticles is mentioned in DE 197 26 282.1. The absorption of the nanoparticles can be analyzed by means of in vitro tests of highly pure cell material. DE 199 12 798 C1 describes methods by means of which any cell from tissue material can be cultivated. Due to these methods, the chemical design of the particles can be such that a large amount thereof is absorbed into certain tumor cells. Methods for increasing the efficacy of therapeutic substances by coupling them to nanoparticles as carrier systems are also known and are object of research. In DE 10059151 A, for example, the substances are coupled by ionic interactions, wherein the conjugate is to be accumulated in the tumor tissue. The therapeutic substance, however, is not released within the cells, but in the interstitium. Transfer of nanoparticles in tumor cells with the help of antibodies or peptides (e.g. TAT peptide) is also known. That kind of transfer, however, only leads to a comparatively low accumulation of nanoparticles in tumor cells and consequently, it cannot be used for therapeutic purposes.

The present invention aims at providing compositions and uses of said compositions for the treatment and prophylaxis of cancer diseases.

Said aim is achieved by the pharmaceutical composition according to claim 1 as well as by the uses off said pharmaceutical composition.

Further advantageous embodiments result from the dependent claims, the examples as well as from the figures and the description.

The present invention relates to pharmaceutical compositions consisting of nanoparticles having a high affinity to degenerated cells, of at least one therapeutically active substance, in particular an anti-cancer drug and of at least one pharmacologically acceptable carrier, excipient and/or solvent.

The substances conventionally used in galenics (pharmaceutical technology) may also be used as pharmacologically acceptable carriers, excipients and/or solvents, wherein fluid pharmaceutical compositions are preferred.

Water or physiological saline can be used as solvents. If necessary, cosolvents such as ethanol in a quantity of up to 10 volume % can be used.

More particularly, said pharmaceutical compositions are solutions for infusion or injection. Such solutions of the nanoparticles, for example in physiological saline, are suitable for interstitial or respectively intratumoral application. Furthermore, intraarterial or intravenous application allows for a systemic therapy, affecting the whole body, of non-solid and/or metastasizing types of tumors.

In this context, the nanoparticles and the at least one therapeutic substance, in particular the at least one anti-cancer drug, don't necessarily have to be contained in one single solution, preferably a solution for injection or infusion. The pharmaceutical composition according to the invention can also be composed of two solutions, wherein one solution contains the nanoparticles and the other solution contains the at least one therapeutically active substance, in particular the at least one anti-cancer drug, and both solutions can be applied at the same time.

Surprisingly it has been found that the nanoparticles described herein are capable of carrying therapeutic substances, in particular anti-cancer drugs, into degenerated cells, a factor which is essential to the invention. The term degenerated cells refers to oncogene cells, tumor cells and cancer cells, that is cells which are completely degenerated or are on their way to complete degeneration. Thus, the term degenerated cells refers to cells with uncontrolled proliferation. Therefore, the therapeutic substances, particularly anti-cancer drugs, are much better absorbed by the degenerated cells if the nanoparticles described herein are present than if the nanoparticles are absent. Due to the improved absorption of the therapeutic substances into the degenerated cells, the activity of said substances, particularly anti-cancer drugs, is significantly improved and the side effects of said substances are reduced.

Increase in activity means that the same amount of therapeutically active substance, particularly anti-cancer drug, is more efficient if the nanoparticles are present than if they are absent. Reduction of the side effects of therapeutic substances, particularly anti-cancer drugs, is intended to mean that, if nanoparticles are present, the damage to healthy cells is reduced with respect to the absence of nanoparticles, while the efficacy or the quantity of anti-cancer drug remains the same.

Thus, the increase in efficacy is based on the prerequisite that the therapeutic substance can be absorbed into the cell simultaneously with the transfer of a large volume of nanoparticles into the cells. Evidently, the invagination of the cell membrane as a consequence of the particle formation results in at least partial elimination of the transmembrane passage control and thus in the formation of a completely new insertion channel for therapeutically active substances. In this context, it is advantageous if a local increase in the concentration of nanoparticles and therapeutic substance, particularly anti-cancer drug, in the interstitium can be achieved. This may for example be realized by interstitial administration of the mixture or by appropriate accumulation strategies, such as controlled release, recognition of receptors or of other biomolecules which are recognized by ligands on the particle surface (targeting). It is also possible to systemically apply the therapeutic substance subsequent to the interstitial administration of the nanoparticles. Intracellular absorption of the nanoparticles occurs within hours to days; consequently, the substance can also be administered several times during the phase of endocytosis. A systemic administration of the substance is in particular required if the substance has to be metabolized.

The nanoparticles should have a positive surface charge, due to the fact that such nanoparticles are particularly well absorbed by degenerated cells, particularly cancer cells.

A surface charge on the nanoparticles which is positive under physiological conditions can be achieved by providing the nanoparticles with a coating which can be positively polarized and/or positively ionized.

Such coating which can be positively polarized and/or positively ionized can be obtained by coating the nanoparticles with substances which can be positively polarized and/or positively ionized. Such substances may for example contain amino groups or protonizable nitrogen atoms which are present in protonized form at a corresponding pH.

Positive surface charge is intended to mean the positively charged surface or a surface which can be positively charged or positively polarized of each nanoparticle, wherein, under physiological conditions, the surface of the nanoparticles should be such that it is positively polarized or positively charged.

In a preferred embodiment, the surface or coating, which is positively charged, can be positively charged or can be positively polarized, is covered by a protective layer compensating or even overcompensating for the positive charges so that an overall neutral or even negatively charged outer surface is obtained. In the event that the coating, which is positively charged or can be positively polarized, is sufficiently stable to avoid decomposition by the body tissue or tumor tissue, said outer layer compensating for the positive charges is not required. In a preferred embodiment, the nanoparticles are provided with a coating consisting of polycondensed aminosilanes and possibly with an additional coating comprising the carboxylate groups compensating for the positive charges.

Due to the fact that slow biodegradation is desired, the coating which is positively charged or can be positively polarized or positively charged preferably consists of biologically stable or respectively biologically inert substances, such as polymers.

The following polymers may be used as biostable polymers: polyacrylamide, polyacrylonitriles, polyamides, polyetheramides, polyethylen amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM rubbers, fluorosilicones, carboxymethyl chitosans, polyaryletherether ketones, polyetherether ketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones such as polysiloxanes, polydimethylsiloxanes, polyvinyl halogens and copolymers, cellulose ethers, cellulose triacetates, chitosans and copolymers and/or mixtures of said substances.

The biologically stable polymers should be provided with a sufficient amount of groups which are positive or can be positively polarized or positively charged such as amino groups or nitrogen atoms. Usually, the positively charged coating is provided with an average of at least 50, preferably at least 100 and particularly preferred at least 500 cationic groups per nanoparticle, which groups can be positively polarized and/or positively charged, such as amino groups.

In preferred embodiments, said coating consists of monomeric aminosilanes, such as 3-aminopropyltriethoxysilane, 2-aminoethyl-3-aminopropyltrimethoxysilane, trimethoxysilyl-propyl-diethylentriamine or N-(6-aminohexyl)-3-aminopropyltrimethoxysilane, which are polycondensed according to known procedures in order to achieve the necessary stability. Suitable methods are described, for instance, in DE 19614136 A or DE 19515820 A.

In order to compensate for the charge and to increase cell discrimination, the positively charged layer or coating can be covered with an additional coating of preferably biologically degradable polymers or respectively biodegradable substances.

The following biodegradable polymers are preferably used: polyvalerolactone, poly-ε-decalactone, polylactonic acid, polyglycolic acid, polylactide, polyglycolides, copolymers from the polylactides and polyglycolides, poly-ε-caprolactone, polyhydroxybutyric acid, polyhydroxybutyrate, polyhydroxyvalerate, polyhydroxybutyrate-co-valerate, poly(1,4-dioxane-2,3-dione), poly(1,3-dioxane-2-dione), poly-para-dioxanone, polyanhydrides such as polymaleic acid anhydrides, polyhydroxymethacrylate, fibrin, polycyanoacrylate, polycaprolactone dimethylacrylate, poly-β-maleic acid, polycaprolactone butyl acrylate, multiblock polymers, e.g. from oligocaprolactonedioles and oligodioxanonedioles, polyetherester multiblock polymers such as PEG and poly(butylene terephthalate), polypivotolactones, polyglycolic acid trimethyl carbonates, polycaprolactone glycolides, poly(γ-ethylglutamate), poly(DTH-iminocarbonate), poly(DTE-co-DT-carbonate), poly(bisphenol A-iminocarbonate), polyorthoesters, polyglycolic acid trimethyl carbonate, polytrimethyl carbonate, polyiminocarbonates, poly(N-vinyl)-pyrrolidone, polyvinyl alcohols, polyesteramides, glycolated polyesters, polyphosphoesters, polyphosphazenes, poly[(p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, carrageenans, fibrinogen, starch, collagen, protein based polymers, polyamino acids, synthetic polyamino acids, zein, modified zein, polyhydroxyalkanoates, pectic acid, actinic acid, modified and non modified fibrin and casein, carboxymethyl sulfate, albumin, hyaluronic acid, chitosan and derivatives thereof, heparan sulfates and derivates thereof, heparins, chondroitin sulfate, dextran, β-cyclodextrins, alginates, glycosaminoglycans, saccharides, polysaccharides, proteoglycans, glycoproteins, copolymers with PEG and polypropylene glycol, gum arabic, guar, gelatin, collagen N-hydroxysuccinimide, phospholipids, modifications and copolymers and/or mixtures of the aforementioned substances.

Polymers or copolymers based on α-hydroxycarboxylic acids such as polylactic acid, polylactides, polyglycolic acid, polyglycolides and copolymers thereof are particularly preferred. Further preferred are polyols (e.g. polyethylene glycol) and polyacids such as polyacrylic acids and carbohydrates and sugar, particularly dextrans.

In other preferred embodiments the inventive nanoparticles are further provided or respectively covered with a third coating. The coatings may serve as protective sheath, barrier layer or for cell discrimination purposes.

A cell specific coating increases the affinity of the nanoparticles to certain cells, such as certain bacteria cells or certain tumor cells and thus serves for cell discrimination. Preferably, such cell specific nanoparticles accumulate in cells to which they have an increased affinity, due to the functionality on their surface, and are therefore tumor specific. Due to said technology, it is, for example, possible to design tumor specific nanoparticles for certain types of cancer.

In order to further increase the affinity to certain cells, polyclonal antibodies, monoclonal antibodies, humanized antibodies, human antibodies, chimeric antibodies, recombinant antibodies, bispecific antibodies, antibody fragments, aptamers, Fab fragments, Fc fragments, peptides, peptidomimetics, gap-mers, ribozymes, CpG oligomers, DNA-zymes, riboswitches and/or lipids can be coupled to and/or attached to and/or integrated into the outer layer or sheath of the nanoparticles. The compounds are designed such that they are capable of recognizing certain cells, such as tumor cells, and further increase the cell discrimination of the nanoparticles.

The nanoparticles themselves preferably consist of a magnetic material, a ferromagnetic, antiferromagnetic, ferrimagnetic, antiferrimagnetic, or superparamagnetic material, further preferred of iron oxides, in particular superparamagnetic iron oxides or of pure iron provided with an oxide layer. Such nanoparticles can be heated by a magnetic alternating field. The tissue containing the nanoparticles can be heated to more than 50° C. Such high temperatures can be achieved due to the fact that up to 1000 pg and more of iron in form of the nanoparticles can be absorbed per tumor cell.

Preferably, the nanoparticles consist of iron oxides and particularly of magnetite ($Fe_3O_4$), maghemite ($\gamma$-$Fe_2O_3$) or mixtures of these two oxides and are preferably superparamagnetic. In general, the preferred nanoparticles can be represented by the formula $FeO_x$, wherein X represents a number from 1 to 2. It is, however, also possible to incorporate the nanoparticles in a non-magnetic material, such as silicon oxide ($SiO_2$) (see below). Preferable, the nanoparticles have a diameter of less than 500 nm. Preferably, the nanoparticles have a medium diameter of 15 nm or are preferably in a size range of 1-100 nm and particularly preferred in the range of 10-20 nm.

In addition to the magnetic materials of the formula $FeO_x$, wherein X is a number in the range of 1.0 to 2.0, materials of the general formula $M(II)Fe_2O_4$ with M=Co, Ni, Mn, Zn, Cu, Cd, Ba or other ferrites can also be used according to the invention. Preferably, metal atoms which differ from iron atoms are contained in a quantity of no more than 70 metal atom %, particularly no more than 35 metal atom %. Preferably, the nanoparticles consist to more than 98% per weight of iron oxide, containing both Fe(III) and Fe(II) in a ratio of preferably 1:1 to 1:3. Additionally, silica or polymer particles, into which the magnetic materials such as those mentioned herein are incorporated and/or to which they are attached, are also suitable.

The nanoparticle cores used may also consist of non-magnetic materials. For example, nanoparticles from polymers (e.g. PLGA, polyacrylamide, polybutyl cyanoacrylate), metals as well as from all oxidic materials (e.g. MgO, CaO, $TiO_2$, $ZrO_2$, $SiO_2$, $Al_2O_3$) may be used. Due to the fact that the capacity to perform endocytosis does not depend on the core of the particles, but on the sheath, any material which can be coated with tumor specific sheaths by means of the above described methods is suitable according to the invention.

Preferably, the nanoparticle or nanoscale particles have an average particle diameter of no more than 100 nm, preferably no more than 50 nm and particularly preferred no more than 30 nm. Preferably, the medium particle diameter is of 1-40 nm, further preferred of 3-30 nm and particularly preferred of 5-25 nm.

Surprisingly, such nanoparticles are very well suited for the transfer of therapeutic substances into certain cell types thereby causing a significant increase in the efficacy of the therapeutic substances. Said therapeutic substances are preferably anti-cancer drugs, cytostatics, cytostatic agents, anti-proliferative agents, antiphlogistic agents, anti-migration agents, antiangiogenic agents, anti-inflammatory agents, antibacterial agents and/or microtubule inhibitors.

Alkylation means, antibiotics with cytostatic characteristics, antimetabolites, microtubule inhibitors and topoisomerase inhibitors, compounds and other cytostatics containing platinum such as asparaginase, tretinoin, alkaloids, podophyllotoxins, taxanes and miltefosine®, hormones, immunomodulators, monoclonal antibodies, signal transductors (molecules for signal transduction) and cytokins can be used as cytotoxic and/or cytostatic compounds, i.e. chemical compounds having cytotoxic and/or cytostatic characteristics.

Examples for alkylation means include amongst others: chlorethamine, cyclophosphamide, trofosfamide, ifosfamide, melphalan, chlorambucil, busulfan, thiotepa, carmustine, lomustine, dacarbazine, procarbazine, temozolomide, treosulfan, estramustine and nimustine.

Examples for antibiotics having cytostatic characteristics include daunorubicin and liposomal daunorubicin, doxorubicin (adriamycin), dactinomycin, mitomycin C, bleomycin, epirubicin (4-epi-adriamycin), idarubicin, dactinomycin, mitoxantrone, amsacrine and actinomycin D.

Methotrexate, 5-fluorouracil, 6-thioguanine, 6-mercaptopurine, fludarabine, cladribine, pentostatin, gemcitabine, cytarabine, azathioprine, raltitrexed, capecitabine, cytosine arabinoside, thioguanine and mercaptopurine can be mentioned as examples for antimetabolites (antimetabolic agents).

Vincristine, vinblastine, vindesine, etoposide as well as teniposide are classified as alkaloids and podophyllotoxins. In addition, compounds containing platinum can be used according to the invention. Cisplatin, carboplatin and oxaliplatin are examples for compounds containing platinum. Among the microtubule inhibitors are counted for example alkaloids such as vinca alkaloids (vincristine, vinblastine, vindesine, vinorelbine) and paclitaxel (Taxol®) as well as derivatives of paclitaxel. Examples for topoisomerase inhibitors include etoposide, teniposide, camptothecin, topotecan and irinotecan.

Paclitaxel and docetaxel are examples for taxane compounds and the other cytostatic agents (other cytostatics) include for example hydroxycarbamide (hydroxyurea), imatinib, Miltefosine®, amsacrine, topotecan (topoisomerase-I inhibitor), pentostatin, bexarotene, tretinoin and asparaginase. Among the representatives of the compound class of monoclonal antibodies are among others trastuzumab (also known as Herceptin®), alemtuzumab (also known as MabCampath®) and rituximab (also known as MabThera®).

According to the invention, hormones such as for example glucocorticoids (prednisone), estrogens (fosfestrol, estramustine), LHRH (buserelin, goserelin, leuprorelin, triptorelin), flutamide, cyproterone acetate, tamoxifen, toremifen, aminoglutethimide, formestane, exemestane, letrozole and anastrozole can also be used. Among the classes of immunomodulators, cytokines, antibodies and signal transductors are counted interleukin-2, interferon-α, erythropoietin, G-CSF, trastuzumab (Herceptin®), rituximab (MabThera®), gefitinib (Iresse), ibritumomab (Zevalin®), levamisole as well as retinoids.

Further possible therapeutic substances include: actinomycin D, aminoglutethimide, anthracyclines, aromatase inhibitors, antiestrogens, buserelin, folic acid antagonists, goserelin, hormone antagonists, hycamtin, hydroxyurea, mitosis inhibitors, tamoxifen, testolactone, sirolimus (rapamycin), everolimus, pimecrolimus, somatostatin, tacrolimus, roxithromycin, daunamycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, 4-hydroxyoxycyclophosphamide, trofosfamide, bendamustine, thymosin α-1, aclarubicin, fludarabine-5′-dihydrogenphosphate, antagonists of purine and pyrimidine bases, hydroxycarbamide, aldesleukin, pegaspargase, letrozole, adriamycin, azithromycin, spiramycin, cepharanthine, epothilone A and B, mitoxantrone, azathioprine, mycophenolate mofetil, c-myc antisense, b-myc antisense, betulinic acid, camptothecin, camptothecin derivatives, melanocyte stimulating hormone (α-MSH), activated protein C, IL 1-β inhibitor, fumaric acid and esters thereof, dermicidin, calcipotriol, tacalcitol, lapachol, β-lapachone, podophyllotoxin, betulin, podophyllic acid 2-ethylhydrazide, molgramostim (rhuGM-CSF), peginterferon α-2b, lenograstim (r-HuG-CSF), filgrastim, macrogol, dacarbazine, cephalomannine, trastuzumab, exemestane, basiliximab, daclizumab, selectin (cytokine antagonist), CETP inhibitor, cadherins, cytokinin inhibitors, COX-2 inhibitor, angiopeptin, ciprofloxacin, fluroblastin, bFGF antagonists, probucol, prostaglandins, 1,11-dimethoxycanthin-6-one, 1-hydroxy-11-methoxycanthin-6-one, scopoletin, colchicine, NO donors, pentaerythrityl tetranitrate, sydnoimines, S-nitroso derivatives, staurosporine, β-estradiol, α-estradiol, estriol, estrone, ethinyl estradiol, fosfestrol, medroxyprogesterone, estradiol cypionates, estradiol benzoates, tranilast, kamebakaurin, verapamil, tyrosine kinase inhibitors (tyrphostins), ciclosporin A, paclitaxel and derivatives thereof such as 6-α-hydroxy-paclitaxel, baccatin, taxotere, mofebutazone, acemetacin, diclofenac, lonazolac, dapsone, o-carbamoyl-phenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterol, ademetionine, myrtecaine, polidocanol, nonivamide, levomenthol, benzocaine, aescin, ellipticine, D-24851 (Calbiochem), colcemid, cytochalasin A-E, indanocine, nocodazole, bacitracin, vitronectin receptor antagonists, azelastine, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF 1, active agents from the group of antibiotics such as cefadroxil, cefazolin, cefaclor, cefoxitin, tobramycin, gentamicin, penicillins, dicloxacillin, oxacillin, sulfonamides, metronidazole, antithrombotics, argatroban, aspirin, abciximab, synthetic antithrombin, bivalirudin, coumadin, enoxaparin, GpIIb/IIIa platelet membrane receptor, antibodies to factor Xa inhibitor, heparin, hirudin, r-hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, NF-kB or Bcl-xL antisense oligonucleotides, halofuginone, nifedipine, tocopherol, molsidomine, tea polyphenols, epicatechin gallate, epigaliocatechin gallate, boswellic acids and derivatives thereof, leflunomide, anakinra, etanercept, sulfasalazine, etoposide, tetracycline, triamcinolone, mutamycin, procainimide, retinoic acid, quinidine, disopyrimide, flecainide, propafenone, sotalol, amiodarone, natural and synthetically obtained steroids such as bryophyllin A, inotodiol, maquiroside A, ghalakinoside, mansonine, strebloside, hydrocortisone, betamethasone, dexamethasone, fenoprofen, ibuprofen, indomethacin, naproxen, phenylbutazone, acyclovir, ganciclovir, zidovudine, antimycotics, clotrimazole, flucytosine, griseofulvin, ketoconazole, miconazole, nystatin, terbinafine, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolides, 4,7-oxycycloanisomelic acid, baccharinoids B1, B2, B2 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrine, taxamairin A and B, regenilol, triptolide, cymarin, apocymarin, aristolochic acid, anopterin, hydroxyanopterin, anemonin, protoanemonin, berberine, cheliburin chloride, cicutoxin, sinococulin, combrestratin A and B, cudraisoflavone A, curcumin, dihydronitidine, nitidine chloride, 12-beta-hydroxypregnadiene-3,20-dione, bilobol, ginkgol, ginkgolic acid, helenalin, indicine, indicine-N-oxide, lasiocarpine, inotodiol, glycoside 1a, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidin, oxoushinsunine, aristolactam-AII, periplocoside A, deoxypsorospermin, psychorubin, ricin A, sanguinarine, manwu wheat acid, methylsorbifolin, chromones of spathelia, stizophyllin, akagerine, dihydrousambaraensine, hydroxyusambarine, strychnopentamine, strychnophylline, usambarine, usambarensine, daphnoretin, lariciresinol, methoxylariciresinol, syringaresinol, umbeliiferone, afromoson, acetylvismione B, desacetylvismione A, vismione A and B.

Thus, it is essential to the invention that the at least one therapeutically active substance is administered in combination with cell-internizable nanoparticles which, to a large extent, are absorbed by the tumor cells by means of endocytosis. Nanoparticles, such as those described, for example, in DE 197 26 282 A are absorbed to a higher extent by tumor cells than by normal cells. As could be shown by tests with iron oxide nanoparticles in vitro, in certain tumor cell lines more than 1000 pg/cell iron are absorbed in form of nanoparticles. For said purpose, the nanoparticles are transferred into the cells in large volumes, as could be demonstrated by electron microscope analysis. In tests in vitro it has now surprisingly been found that the administration of pharmaceutical compounds of said nanoparticles and at least one therapeutically active substance, in particular a cytostatic or an anti-cancer drug, leads to an increase in the efficacy of the administered substance. Said effect has also been observed when no bond (covalent, ionic or adsorptive) was existent between the nanoparticles and the cytostatic. A bond between cytostatic and nanoparticle only influences said results if, due to the binding reaction, the cytostatic loses its efficacy, or if the bond is strong enough to prevent the release of the cytostatic upon intracellular absorption.

Thus, the pharmaceutical compositions consisting of said nanoparticles and at least one therapeutically active substance are perfectly suited for the prophylaxis and treatment of cancer diseases, ulcers, tumors, carcinomas as well as cells which are defective in their proliferation.

Examples for types of cancers and tumors, for which the inventive compositions consisting of nanoparticle and active substance can be used include the following: adenocarcinomas, choroidal melanoma, acute leukemia, acoustic neurinoma, ampullary carcinoma, anal carcinoma, astrocytomas, basal cell carcinoma, pancreatic cancer, connective tissue tumor, bladder cancer, bronchial carcinoma, non-small cell bronchial carcinoma, breast cancer, Burkitt's lymphoma, corpus carcinoma, CUP syndrome, cancer of the large intestine, cancer of the small intestine, tumors of the small intestine, ovarian cancer, endometrial carcinoma, ependymoma, epithelial cancers, Ewing tumors, gastrointestinal cancers, gall bladder cancers, gall carcinomas, uterine cancer, cervical cancer, glioblastomas, gynecological cancers, tumors of ear, nose and throat, hematological neoplasias, hairy cell leukemia, urethral cancer, skin cancer, brain tumors (gliomas), brain metastases, testicular cancer, hypophysis tumor, carcinoids, Kaposi's sarcoma, laryngeal cancer, germ cell tumor, bone cancer, colorectal carcinoma, head and neck tumors (tumors situated in the region of the neck, nose and ears), colon carcinoma, craniopharyngiomas, cancer in the area of the mouth and on the lip, liver cancer, liver metastases, leukemia, tumor of the eyelid, lung cancer, malignant lymphoma (Hodgkin/Non-Hodgkin), lymphomas, stomach cancer, malignant melanoma, malignant neoplasma, malignomas of the gastrointestinal tract, breast carcinoma, rectal cancer, medulloblastomas, melanoma, meningiomas, Hodgkin's disease, mycosis fungoides, nose cancer, neurinoma, neuroblastoma, kidney cancer, renal cell carcinoma, Non-Hodgkin's lymphomas, oligodendroglioma, esophageal carcinoma, osteolytic tumors and osteoblastic tumors, osteosarcoma, ovarian carcinoma, pancreatic carcinoma, penile carcinoma, plasmacytoma, squamous cell carcinoma of the head and the neck, prostate cancer, throat cancer, rectal carcinoma, retinoblastoma, vaginal cancer, thyroid carcinoma, Schneeberg lung cancer, esophageal cancer, spinocellular carcinoma, T-cell lymphoma (Mycosis fungoides), thymoma, tube carcinoma, eye tumors, urethral carcinoma, urological tumors, urothelial carcinoma, vulvar carcinoma, wart appearance, soft tissue tumors, soft tissue sarcoma, Wilm's tumor, cervical carcinoma and tongue cancer.

Solid tumors are particularly preferred. Prostate carcinomas, brain tumors, sarcomas, cervical carcinomas, ovarian carcinomas, breast carcinomas, bronchial carcinomas, melanomas, head and neck tumors, esophageal carcinomas, rectal carcinomas pancreatic, bladder and renal carcinomas, metastases in the liver, in the brain and in the lymph nodes are particularly preferred.

Furthermore, the application and the use of the inventive compositions in combination with conventional hyperthermia, magnetic fluid hyperthermia or respectively thermotherapy with magnetic fluids, radiotherapy and/or in combination with conventional chemotherapy are particularly preferred. Thus, conventional methods for the treatment of cancers are advantageously complemented by the inventive compositions.

Accordingly, the present invention is also directed to combinations of an inventive pharmaceutical composition and hyperthermia, thermotherapy, radiotherapy and/or chemotherapy.

Examples for such combinations include the use of an inventive pharmaceutical composition in combination with magnetic fluid hyperthermia or respectively thermotherapy with magnetic fluids. For this purpose, an alternating magnetic field acts as external stimulation for triggering different relaxation processes of the nanoparticles, provided that superparamagnetic nanoparticles are used. Amongst others, said processes result in the nanoparticles and their surroundings being heated. According to the invention, said processes triggered by the alternating magnetic field are used for heating the degenerated cells, whereby the therapeutically active substance can cause the death of the concerned cell even more rapidly.

Thus, the pharmaceutical compositions are used both for the treatment and the prophylaxis of diseases characterized by degenerated cell species or foreign cells and in which the properties of the inventive nanoparticles regarding the discrimination between foreign or respectively degenerated and healthy self cells and regarding the transfer of therapeutically active substances into said cells can be advantageously used. Degenerated cells are in particular cancer cells, or respectively cells which are defective in their proliferation and stenotic or restenotic tissue. Foreign cells include in particular bacteria.

The efficacy of the active ingredients is increased by the capacity of the nanoparticles to transfer active ingredients into degenerated cells. If the application of the pharmaceutical composition comprising nanoparticles and therapeutically active substance is additionally combined with radiotherapy or chemotherapy, or with hyperthermia or hyperthermia and chemotherapy or with hyperthermia and radiotherapy, the efficacy of the treatment can be further improved.

According to the invention, the efficacy of the active ingredients is thus increased as a consequence of an increased local, locoregional or intracellular concentration of active ingredients and the systemic toxicity and side effects of the therapeutically active substances are reduced.

EXAMPLES

Example 1

Increase in the Efficacy of the Cytostatic Mitomycin (In Vitro)

The increase in the efficacy of mitomycin for the treatment of tumor cells could be proved by tests in vitro. The tests in vitro were performed with the glioblastoma human cell line RUSIRS 1 (brain tumor). The glioblastoma cells were taken from tumor tissue of a patient and cultivated as described in DE 199 12 798 C1. $2 \times 10^6$ RUSIRS 1 cells, respectively, were prepared in a 75 cm$^3$ cell culture bottle with 25 ml of cell culture medium (D-MEM+20% FBS+1.2 ml of pyruvate) for testing the efficacy of the mitomycin/nanoparticle mixture. 136 pl of magnetic fluid MFL AS M01

(iron oxide nanoparticle coated with polycondensed N-(2-aminoethyl)-3-(trimethoxysilyl)propylamine, manufacturer: Mag Force Nanotechnologies GmbH, Berlin, Germany) ($c_{Fe}$=2 mol/l) and 390 µl of mitomycin solution (1 mg/ml in 0.9% NaCl) were added to said cell suspension. Before being added to the cells, the samples of the nanoparticles were heated to 37° C. for 15 minutes and allowed to rest at RT for 10 minutes. A control sample with mitomycin but without nanoparticles was prepared in the same way.

Figure 1:
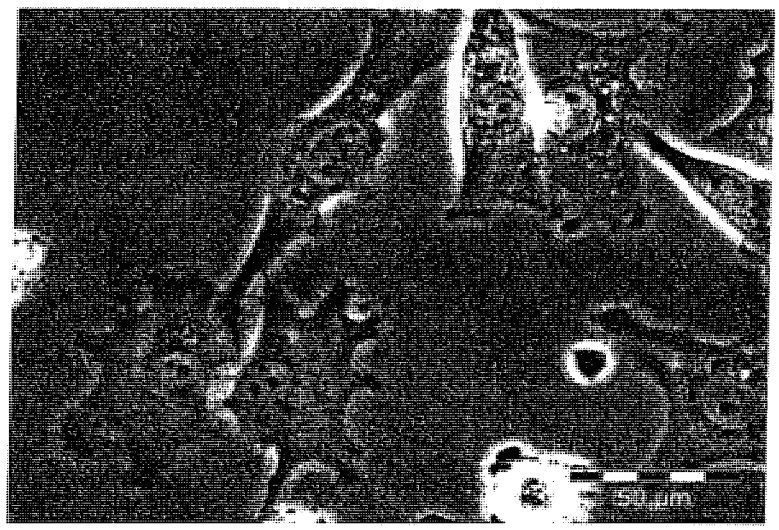
FIG. 1 shows RUSIRS1 cells 3 hrs after the addition of mitomycin in 0.9% NaCl
Figure 2:
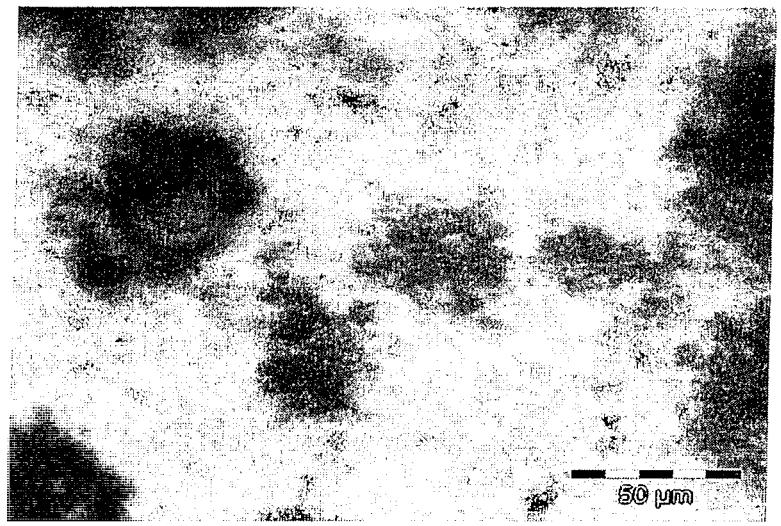
FIG. 2 shows RUSIRS1 cells 3 hrs after the addition of mitomycin in 0.9% NaCl+nanoparticle
Figure 3:
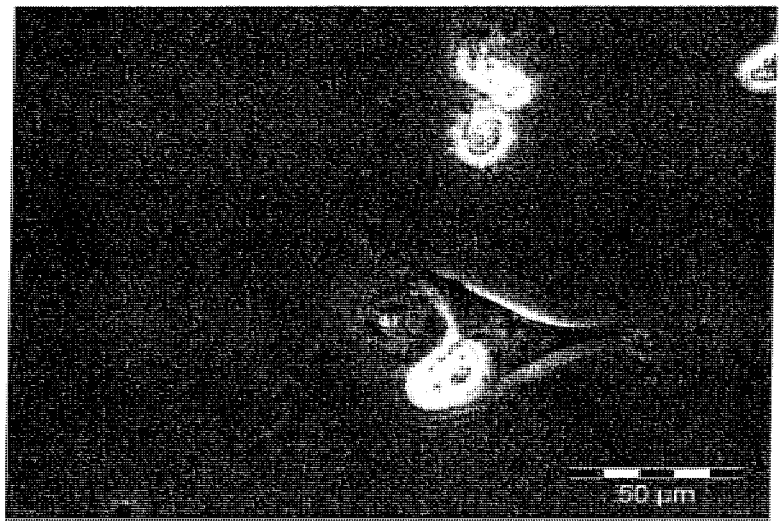
FIG. 3 shows RUSIRS1 cells 24 hrs after the addition of mitomycin in 0.9% NaCl
Figure 4:
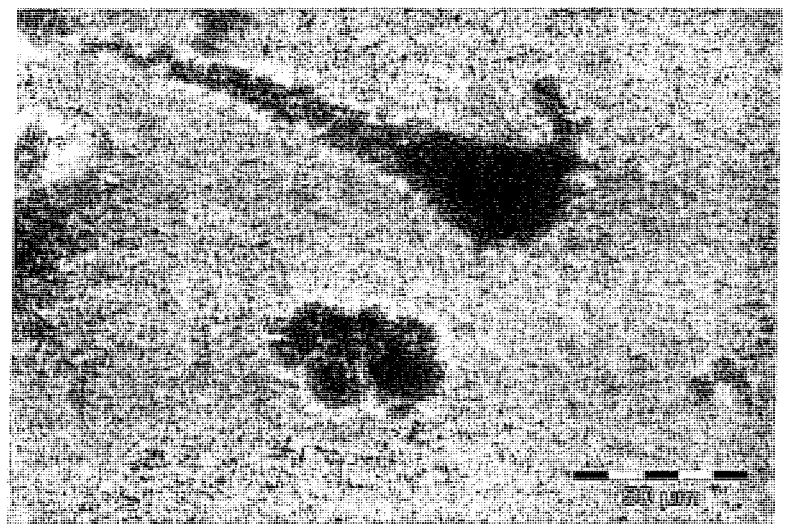
FIG. 4 shows RUSIRS1 cells 24 hrs after the addition of mitomycin in 0.9% of NaCl+nanoparticle
Figure 5:
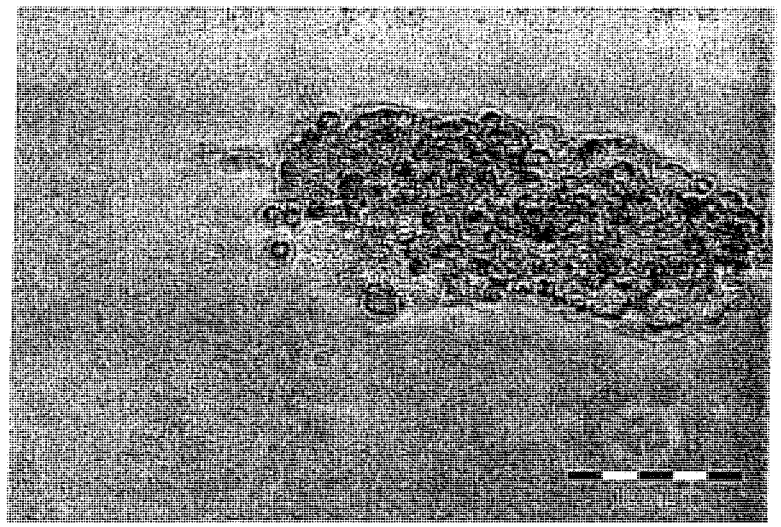
FIG. 5 shows RUSIRS1 cells 48 hrs after the addition of mitomycin in 0.9% NaCl
Figure 6:
FIG. 6 shows RUSIRS1 cells 48 hrs after the addition of mitomycin in 0.9% NaCl+nanoparticle

The influence of the nanoparticles on the efficacy of mitomycin can be illustrated by means of FIGS. 1-6. Cells to which nothing but a mitomycin solution had been added only showed significant damage after 48 hrs of incubation. By contrast, cells which were incubated with the cytostatic and the particles already showed significant damage after 3 hrs. The absorption of the iron oxide nanoparticles into the cells can be proven by a brown coloration of the cell. Control experiments showed that the nanoparticles alone (without mitomycin) are also absorbed, but do not cause a similarly high cell damage. Rapid cell damage (after 3 hrs) occurs only if particle and mitomycin are present at the same time. Consequently, mitomycin was also transferred by the endocytosis of the particles, thereby causing significant cell damage.

Example 2

Increase in the Efficacy of the Antibiotic Cefamandole (In Vitro)

Cefamandole (CAS No 30034-03-8) is used to combat bacterial infections. In 2000, an efficacy against cancer cells was surprisingly found on biopsy material of liver metastases (MagForce Nanotechnologies). This substance's potential to combat cancer cells, however, is to be considered to be rather low. Our experiments showed that a destruction of tumor cells (in vitro), usually, can only be achieved by using a concentration of 0.5 mg/ml (concentration in the cell culture medium) or more. It is, however, possible to drastically increase the efficacy of cefamandole in the treatment of tumor cells by the simultaneous application of nanoparticles.

The experiments in vitro were carried out with the cell lines BT20 (breast carcinoma) and WiDr (colon carcinoma). The tumor cells were taken from tumor tissue of a patient and cultivated as described in DE 199 12 798 C1. $2\times10^6$ cells, respectively, were prepared in a 75 cm³ cell culture bottle with 25 ml of cell culture medium (RPMI+10% FBS+1.2 ml of pyruvate for WiDr cells, or respectively BME+10% FBS+pyruvate+5 ml of non-essential amino acids+5 ml glutamine for BT20 cells) for testing the efficacy of the cefamandole/nanoparticle mixture. 136 µl of magnetic fluid MFL AS M01 (iron oxide nanoparticle coated with polycondensed N-(2-aminoethyl)-3-(trimethoxysilyl)propylamine, manufacturer: MagForce Nanotechnologies GmbH, Berlin, Germany) ($c_{Fe}$=2 mol/l) and 390 µl of cefamandole solution (stock solution 1 mg/ml in 0.9% NaCl) were added to said cell suspension. Therefore, the concentration of cefamandole in the cell culture medium (25 ml) was 0.016 mg/ml and thus significantly below the threshold of efficacy of pure cefamandole.

Figure 7:
FIG. 7 shows RUSIRS1 cells after 48 hrs (control)
Figure 8:
FIG. 8 shows BT20 cells after 72 hrs as control with cefamandole but without nanoparticles
Figure 9:
FIG. 9 shows BT20 cells after 72 hrs of incubation with nanoparticles and cefamandole
Figure 10:
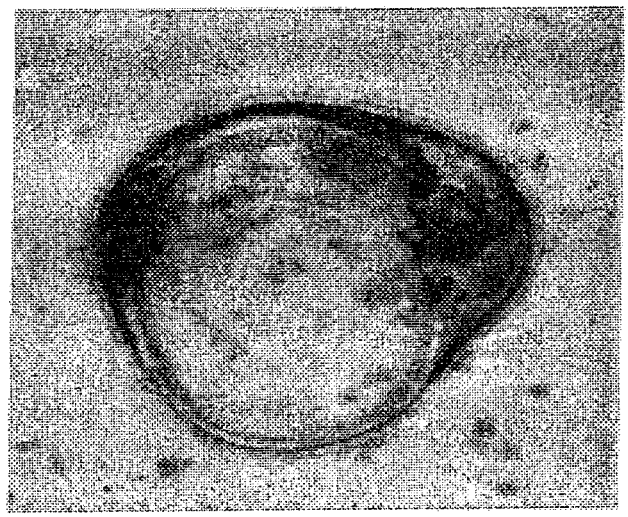
FIG. 10 shows BT20 cells after 72 hrs of incubation with nanoparticles and cefamandole
Figure 11:
FIG. 11 shows WiDr cells after 72 hrs as control with cefamandole but without nanoparticles
Figure 12:
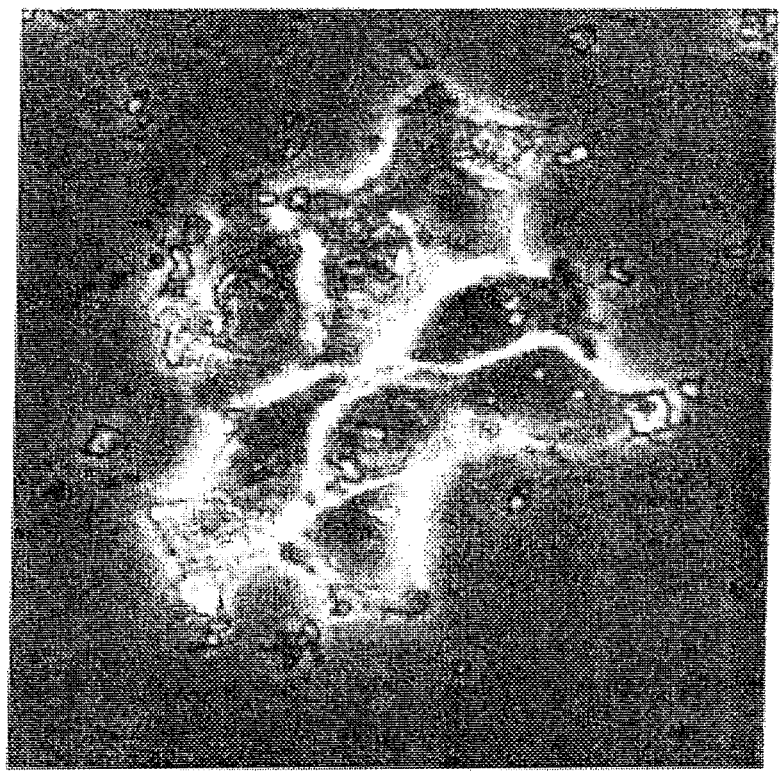
FIG. 12 shows WiDr cells after 72 hrs of incubation with nanoparticles and cefamandole
Figure 13:
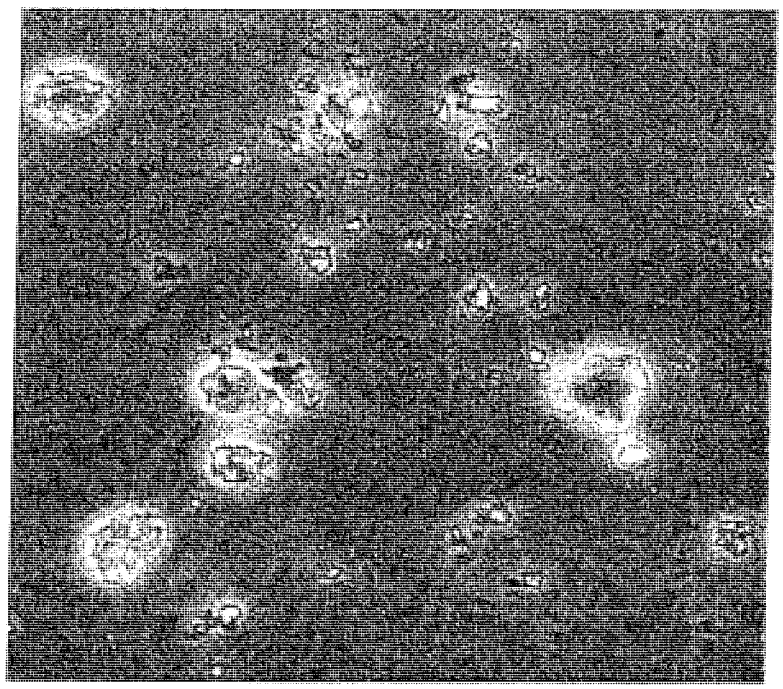
FIG. 13 shows WiDr cells after 72 hrs of incubation with nanoparticles and cefamandole

After 72 hrs of incubation, significant cell damage could be observed, as evidenced by FIGS. 7-12. After 72 hrs, 30.5% of the BT20 cells and 24% of the WiDr cells had died. Neither cefamandole in the selected concentration, nor the nanoparticle alone, are capable of causing cell death (0% of dead cells). Only the combination of cefamandole and nanoparticles leads to said significant damage of the tumor cells which is due to the transfer of cefamandole into the cells.

Example 3

Preparation of a Pharmaceutical Composition Consisting of Nanoparticles, Pharmacological Active Ingredient and Solvent About 1 mg of a cytostatic (or 1 to 10 mmol, preferably 2 to 6 mmol of a cytostatic) is added to one ml of an aqueous dispersion of superparamagnetic iron oxide nanoparticles (iron concentration of 2 ml/l).

In the case that the cytostatic is not sufficiently soluble in water, cosolvents in a quantity of up to 20 volume % of the solution can be used. DMSO, DMS, ethanol, acetic acid ethyl ester or other physiologically acceptable solvents may be used as cosolvents.

Example 4

1 mg of carmustine or 1 mg of cisplatin or 1 mg of epirubicin or 1.5 mg of gemcitabine or 1 mg of imatinib or 0.8 mg of paclitaxel or 1.2 mg of vinblastine or 1 mg of vincristine or 1.5 mg of adriamycin or 1 mg of oxacillin or 1 mg of tetracycline or 1 mg of temozolomide are added to one ml of the magnetic fluid MFL AS M01 (iron oxide nanoparticle coated with polycondensed N-(2-aminoethyl)-3-(trimethoxysilyl)propylamine, manufacturer: MagForce Nanotechnologies AG, Berlin, Germany) ($c_{Fe}$=2 mol/l) and thoroughly mixed.

Example 5

Increase in the Efficacy of the Cytostatic Mitoxantrone (In Vitro)

Primary prostate carcinoma cells were cultivated as described in DE 199 12 798 C1. $2\times10^6$ cells, respectively, were prepared in a 75 cm³ cell culture bottle with 25 ml of cell culture medium for testing the efficacy of the mitoxantrone/nanoparticle mixture. 136 µl of magnetic fluid MFL AS M01 (iron oxide nanoparticle coated with polycondensed N-(2-aminoethyl)-3-(trimethoxysilyl)propylamine, manufacturer: MagForce Nanotechnologies GmbH, Berlin, Germany) ($c_{Fe}$=2 mol/l) and 390 µl of mitoxantrone solution (stock solution 1 mg/ml in 0.9% NaCl) were added to said cell suspension. Significant cell damage could be observed after 72 hrs of incubation. There was evidence for a similar effect when the cytostatics epirubicin and docetaxel (dissolved in polyoxyethylated sorbitol; polysorbate 80) were used.

Example 6

Increase in the Efficacy of the Cytostatic 5-fluorouracil (In Vitro)

Primary rectal carcinoma cells were cultivated as described in DE 199 12 798 C1. $2\times10^6$ cells, respectively, were prepared in a 75 cm³ cell culture bottle with 25 ml of cell culture medium for testing the efficacy of the 5-fluorouracil/nanoparticle mixture. 136 µl of magnetic fluid MFL AS M01 (iron oxide nanoparticle coated with polycondensed N-(2-aminoethyl)-3-(trimethoxysilyl)propylamine, manufacturer: MagForce Nanotechnologies GmbH, Berlin, Germany) ($c_{Fe}$=2 mol/l) and 390 µl of 5-fluorouracil solution (stock solution 1 mg/ml in 0.9% NaCl) were added to said cell suspension. Significant cell damage could be observed after 72 hrs of incubation. There was evidence for a similar effect when the cytostatics irinotecan and oxaliplatin were used.

Example 7

Increase in the Efficacy of the Cytostatic Carboplatin (In Vitro)

Primary bronchial carcinoma cells (non-small cell lung cancer; NSCLC) were cultivated as described in DE 199 12 798 C1. $2 \times 10^6$ cells, respectively, were prepared in a 75 cm³ cell culture bottle with 25 ml of cell culture medium for testing the efficacy of the carboplatin/nanoparticle mixture. 136 μl of magnetic fluid MFL AS M01 (iron oxide nanoparticle coated with polycondensed N-(2-aminoethyl)-3-(trimethoxysilyl)propylamine, manufacturer: MagForce Nanotechnologies GmbH, Berlin, Germany) ($c_{Fe}$=2 mol/l) and 390 μl of carboplatin solution (stock solution 1 mg/ml in 0.9% NaCl) are added to said solution. Significant cell damage could be observed after 72 hrs of incubation. There was evidence for a similar effect when the cytostatics epirubicin and docetaxel (dissolved in polyoxyethylated sorbitol; polysorbate 80) were used.

Examples 8-196

Corresponding to the experiment procedure according to example 2, the following 7 cell lines were tested in vitro with the active ingredients listed in table 1: a) glioblastoma human cell line RUSIRS 1; b) breast carcinoma cell lines BT20; c) colon carcinoma cell line WiDR; d) bronchial carcinoma cells NSCLC, e) rectal carcinoma cells and f) prostate carcinoma cell line DU 145.

In all cases, an increased activity of the cytostatic could be observed. The increase in activity is indicated in parentheses after the respective cytostatic, wherein (+) means an increase of about 5% to 80% and (++) means an increase of 80% to 500%.

TABLE 1 increase in the activity of cytostatics

| glioblastoma human cell line RUSIRS1 | breast carcinoma cell lines BT20 | colon carcinoma cell line WiDr | bronchial carcinoma cells NSCLC | rectal carcinoma cells | prostate carcinoma cell line DU 145 | neuroglioma cell line H4 |
|---|---|---|---|---|---|---|
| letrozole (+) | letrozole (+) | letrozole (+) | letrozole (+) | letrozole (+) | letrozole (+) | letrozole (+) |
| tamoxifen (+) | tamoxifen (+) | tamoxifen (++) | tamoxifen (+) | | tamoxifen (+) | tamoxifen (+) |
| somatostatin (+) | | somatostatin (+) | somatostatin (+) | somatostatin (+) | somatostatin (++) | somatostatin (+) |
| tacrolimus (+) | tacrolimus (+) | | tacrolimus (+) | tacrolimus (+) | tacrolimus (+) | tacrolimus (++) |
| ascomycin (++) | ascomycin (+) | ascomycin (+) | ascomycin (+) | ascomycin (+) | ascomycin (+) | |
| cerivastatin (+) | cerivastatin (+) | cerivastatin (+) | cerivastatin (+) | cerivastatin (++) | cerivastatin (+) | cerivastatin (+) |
| simvastatin (+) | simvastatin (+) | simvastatin (+) | simvastatin (++) | simvastatin (+) | simvastatin (+) | simvastatin (+) |
| bendamustine (+) | bendamustine (+) | | bendamustine (+) | | bendamustine (+) | |
| tobramycin (+) | tobramycin (+) | tobramycin (+) | tobramycin (+) | tobramycin (+) | tobramycin (+) | tobramycin (+) |
| ganciclovir (++) | ganciclovir (+) | ganciclovir (+) | ganciclovir (+) | ganciclovir (+) | ganciclovir (+) | ganciclovir (+) |
| acyclovir (+) | acyclovir (+) | acyclovir (+) | acyclovir (+) | acyclovir (++) | acyclovir (+) | acyclovir (+) |
| ibuprofen (+) | ibuprofen (+) | ibuprofen (++) | ibuprofen (+) | ibuprofen (+) | ibuprofen (+) | ibuprofen (+) |
| paclitaxel (+) | paclitaxel (++) | paclitaxel (+) | paclitaxel (+) | paclitaxel (+) | paclitaxel (+) | paclitaxel (+) |
| diclofenac (+) | | diclofenac (+) | diclofenac (+) | diclofenac (++) | diclofenac (+) | diclofenac (+) |
| azelastine (+) | azelastine (+) | | | azelastine (+) | azelastine (+) | azelastine (+) |
| oxacillin (+) | oxacillin (+) | oxacillin (++) | oxacillin (+) | oxacillin (+) | oxacillin (++) | oxacillin (+) |
| nifedipine (+) | nifedipine (+) | nifedipine (+) | nifedipine (+) | | nifedipine (+) | nifedipine (+) |
| leflunomide (+) | leflunomide (+) | leflunomide (+) | leflunomide (+) | leflunomide (+) | leflunomide (+) | leflunomide (+) |
| tetracycline (+) | tetracycline (+) | tetracycline (+) | tetracycline (+) | tetracycline (++) | tetracycline (++) | tetracycline (+) |
| rapamycin (+) | rapamycin (++) | rapamycin (+) | rapamycin (+) | rapamycin (++) | rapamycin (+) | rapamycin (+) |
| imatinib (+) | imatinib (+) | imatinib (++) | imatinib (+) | imatinib (+) | imatinib (+) | imatinib (+) |
| vincristine (+) | vincristine (++) | vincristine (+) | vincristine (++) | vincristine (++) | vincristine (+) | vincristine (+) |
| gemcitabine (+) | gemcitabine (+) | gemcitabine (+) | gemcitabine (++) | gemcitabine (+) | gemcitabine (+) | gemcitabine (+) |
| cladribine (+) | cladribine (+) | cladribine (++) | cladribine (++) | | cladribine (+) | cladribine (+) |

TABLE 1-continued

| increase in the activity of cytostatics | | | | | | |
|---|---|---|---|---|---|---|
| glioblastoma human cell line RUSIRS1 | breast carcinoma cell lines BT20 | colon carcinoma cell line WiDr | bronchial carcinoma cells NSCLC | rectal carcinoma cells | prostate carcinoma cell line DU 145 | neuroglioma cell line H4 |
| idarubicin (++) | idarubicin (+) | idarubicin (+) | idarubicin (++) | idarubicin (+) | idarubicin (+) | idarubicin (+) |
| busulfan (+) | | busulfan (+) | busulfan (++) | | busulfan (+) | busulfan (+) |
| chlorambucil (+) | chlorambucil (+) | chlorambucil (++) | chlorambucil (+) | chlorambucil (+) | chlorambucil (+) | chlorambucil (++) |
| carmustine (+) | carmustine (+) | carmustine (+) | carmustine (++) | carmustine (+) | carmustine (+) | carmustine (+) |
| cisplatin (+) | cisplatin (+) | cisplatin (+) | cisplatin (++) | cisplatin (+) | cisplatin (+) | cisplatin (++) |

The invention claimed is:

1. A method for increasing the activity of an anti-cancer drug comprising the steps of administering to a patient in need thereof a pharmaceutical composition comprising magnetic nanoparticles having an affinity to degenerated cells, at least one pharmaceutical composition comprising an anti-cancer drug and at least one pharmaceutically acceptable carrier, excipient and/or solvent, wherein the magnetic nanoparticles have a positive surface charge, and comprise a coating of polycondensed aminosilane, wherein the pharmaceutical compositions comprising the magnetic nanoparticles and the at least one anti-cancer drug are administered separately, wherein the magnetic nanoparticles and the at least one anti-cancer drug are present at the same time in the patient, and wherein the increase in activity of the anti-cancer drug occurs without hyperthermia.

2. The method for increasing the activity of an anti-cancer drug according to claim 1, further comprising administering radiation therapy.

3. The method according to claim 1, wherein the nanoparticles comprise iron oxide, magnetite, maghemite or $M(II)Fe_2O_4$, wherein M represents Zn, Cu, Co, Ni, Cd, Ba or Mn.

4. The method according to claim 1, wherein the at least one cancer drug is a cytostatic agent, an antiproliferative agent, an antiangiogenic agent, or a microtubule inhibitor.

5. The method according to claim 1, wherein the at least one cancer drug is selected from the group comprising: actinomycin D, aminoglutethimide, amsacrine, anastrozole, antagonists of purine and pyrimidine bases, anthracyclines, aromatase inhibitors, asparaginase, antiestrogens, bexarotene, bleomycin, buserelin, busulfan, camptothecin derivatives, capecitabine, carboplatin, carmustine, chlorambucil, cisplatin, cladribine, cyclophosphamide, cytarabine, cytosine arabinoside, alkylating cytostatics, dacarbazine, dactinomycin, daunorubicin, docetaxel, doxorubicin (adriamycin), doxorubicin lipo, epirubicin, estramustine, etoposide, exemestane, fludarabine, fluorouracil, folic acid antagonists, formestane, gemcitabine, goserelin, hormones and hormone antagonists, hycamtin, hydroxyurea, idarubicin, ifosfamide, imatinib, irinotecan, letrozole, leuprorelin, lomustine, melphalan, mercaptopurine, methotrexate, mitomycins, mitosis inhibitors, mitoxantrone, nimustine, oxaliplatin, pentostatin, procarbazine, tamoxifen, temozolomide, teniposide, testolactone, thiotepa, thioguanine, topoisomerase inhibitors, topotecan, treosulfan, tretinoin, triptorelin, trofosfamide, vinblastine, vincristine, vindesine, vinorelbine, cytostatically active antibiotics, somatostain, bafilomycin, 4-hydroxyoxycyclophosphamide, bendamustine, thymosin α-1, aclarubicin, fludarabine-5'-dihydrogen phosphate, hydroxycarbamide, aldesleukin, pegaspargase, adriamycin, cepharanthine, epothilone A and B, c myc antisense, b-myc antisense, betulinic acid, camptothecin, melanocyte stimulating hormone (α-MSH), lapachol, β-lapachone, podophyllotoxin, podophyllinic acid 2-ethyl hydrazide, molgramostim (rhuGM-CSF), peginterferon α-2b, lenograstim (r-HuG-CSF), filgrastim, macrogol, cephalomannine, trastuzumab, daclizumab, angiopeptin, fluroblastin, bFGF antagonists, probucol, 1,11-dimethoxyeanthin-6-one, 1-hydroxy-11-methoxycanthin-6-one, scopoletin, colchicine, staurosporine, β-estradiol, α-estradiol, estriol, estrone, ethinyl estradiol, fosfestrol, medroxyprogesterone, estradiol cypionates, estradiot benzoates, tranilast, kamebakaurin, tyrosine kinase inhibitors (tyrphostins), ciclosporin A, paclitaxel and derivatives thereof comprising 6-α-hydroxy paclitaxel, baccatin, elipticine, D-24851, colcemid, cytochalasin A-E, indanocine, nocodazole, bacitracin, vitronectin receptor antagonists, free nucleic acids, nucleic acids incorporated into virus transmitters, DNA and RNA fragments, plasminogen activator inhibitor-1, plasminogen activator inhibitor-2, antisense oligonucleotide, VEGF inhibitors, thioprotease inhibitors, interferon α, β and γ, NF-kB or Bcl-xL antisense oligonucleotides, halofuginone, nifedipine, tocopherol, tea polyphenols, epicatechin gallate, epigallocatechin gallate, boswellic acids and derivatives thereof, mutamycin, retinoic acid, natural and synthetically obtained steroids comprising bryophyllin A, inotodiol, maquiroside A, ghalakinoside, mansonine, strebloside, hippocaesculin, barringtogenol-C21-angelate 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrine, taxamairin A and B, regenilol, triptolide, anopterin, hydroxyanopterin, berberine, cheliburin chloride, cicutoxin, sinococuline, combrestatin A and B, cudraisoflavone A, curcumin, dihydronitidine, nitidine chloride, 12-beta-hydroxypregnadiene-3,20-dione bilobol, helenalin, indicine, indicine-N-oxide, lasiocarpine, justicidin A and B, larreatin, malloterin, mallotochromanol, isobutyrylmallotochromanol, marchantin A, maytansine, lycoridicin, margetine, pancratistatin, liriodenine, bisparthenolidine, oxoushinsunine, aristolactam-AII, deoxypsorospermin, psychorubin, ricin A, sanguinarine, manwu wheat acid, methylsorbifolin, chromones of spathelia, stizophyllin, akagerine, dihydrousambaraensine, hydroxyusambarine, strychnopentamine, strychnophylline, usambarine, usambarensine, daphnoretin, lariciresinol, methoxylariciresinol, syringaresinol, umbelliferone, afromoson, acetylvismione B, desacetylvismione A, vismione A and B.

6. The method according to claim 1, wherein the pharmaceutical compositions are present in formulations which are suitable for injection or infusion.

7. The method of claim 1, wherein the coating consists of polycondensed monomeric aminosilanes selected from the group of 3-aminopropyltriethoxysilane, 2-aminoethyl-3-aminopropyltrimethoxysilane, trimethoxysilyl-propyl-diethylentriamine, and N-(6-aminohexyl)-3-aminopropyltrimethoxysilane.

8. The method of claim 1, wherein the coating consists of polycondensed N-(2-aminoethyl)-3-(trimethoxysilyl)propylamine.

* * * * *